US00PP34012P2

(12) United States Plant Patent
Jones

(10) Patent No.: US PP34,012 P2
(45) Date of Patent: Mar. 15, 2022

(54) ***EREMOPHILA* PLANT NAMED 'MSWNERMAS'**

(50) Latin Name: *Eremophila maculata*
Varietal Denomination: MSWNErmas

(71) Applicant: Camelot Nurseries Inc., Glendale, AZ (US)

(72) Inventor: Kelly Jones, Glendale, AZ (US)

(73) Assignee: Camelot Nurseries Inc., Glendale, AZ (US)

( * ) Notice: Subject to any disclaimer, the term of this patent is extended or adjusted under 35 U.S.C. 154(b) by 0 days.

(21) Appl. No.: 17/220,649

(22) Filed: Apr. 1, 2021

(51) Int. Cl.
*A01H 5/00* (2018.01)
*A01H 6/00* (2018.01)
*A01H 6/86* (2018.01)
*A01H 5/02* (2018.01)

(52) U.S. Cl.
USPC ..... Plt./226
CPC ..... *A01H 6/86* (2018.05); *A01H 5/02* (2013.01)

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Eremophila* plant named 'MSWNErmas', characterized by its relatively compact, upright to outwardly spreading plant habit; vigorous growth habit and rapid growth rate; freely branching habit, dense and bushy appearance; acicular dark green-colored leaves; relatively early and freely flowering habit; long flowering period; bright red-colored flowers; and good garden performance.

2 Drawing Sheets

Figure 1:
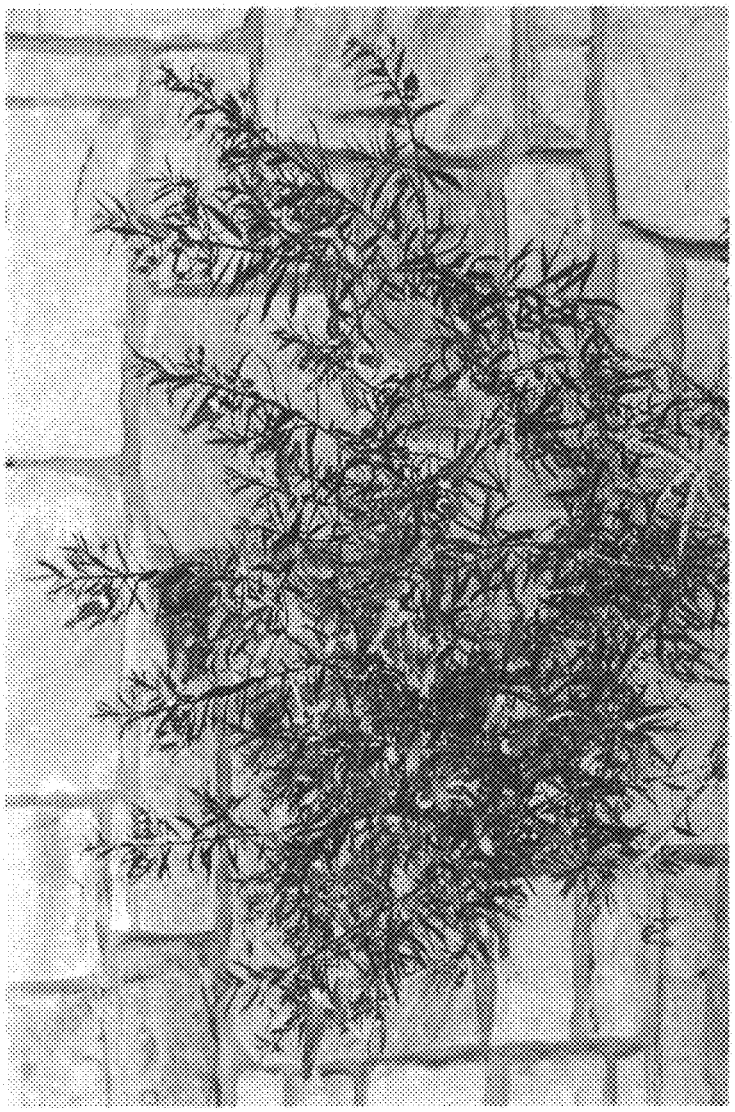

Botanical designation: *Eremophila maculata*.
Cultivar denomination: 'MSWNErmas'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Eremophila* plant, botanically known as *Eremophila maculata*, commonly referred to as Spotted Emu Bush and hereinafter referred to by the name 'MSWNErmas'. The genus *Eremophila* is a member of Scrophulariaceae family and *Eremophila maculata* is endemic to mainland Australia.

The new *Eremophila* plant is a product of a planned breeding program conducted by the Inventor in Glendale, Ariz. The objective of the breeding program is to create new relatively compact and freely flowering *Eremophila* plants with attractive flower coloration and improved low and high temperature tolerance.

The new *Eremophila* plant originated from an open-pollination in March, 2016, in Glendale, Ariz. of *Eremophila*

*maculata* 'Thunder Cloud', not patented, as the female, or seed, parent with an unknown selection of *Eremophila maculata* as the male, or pollen, parent. The new *Eremophila* plant was discovered and selected by the Inventor as a single flowering plant from within the progeny of the stated open-pollination in a controlled environment in Glendale, Ariz. on Aug. 22, 2016.

Asexual reproduction of the new *Eremophila* plant by terminal vegetative cuttings in a controlled environment in Glendale, Ariz. since August, 2018, has shown that the unique features of this new *Eremophila* plant are stable and reproduced true to type in successive generations.

SUMMARY OF THE INVENTION

Plants of the new *Eremophila* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MSWNErmas'. These characteristics in combination distinguish 'MSWNErmas' as a new and distinct *Eremophila* plant:

1. Relatively compact, upright to outwardly spreading plant habit.
2. Vigorous growth habit and rapid growth rate.
3. Freely branching habit, dense and bushy appearance.
4. Acicular dark green-colored leaves.
5. Relatively early and freely flowering habit.
6. Long flowering period.
7. Bright red-colored flowers.
8. Good garden performance.

Plants of the new *Eremophila* differ primarily from plants of the female parent, 'Thunder Cloud' in the following characteristics:

1. Plants of the new *Eremophila* are more compact and denser than plants of 'Thunder Cloud'.
2. Leaves of plants of the new *Eremophila* are acicular whereas leaves of plants of 'Thunder Cloud' are oblong.
3. Plants of the new *Eremophila* flower earlier and for a longer period of time than plants of 'Thunder Cloud'.
4. Flowers of plants of the new *Eremophila* are bright red in color whereas flowers of plants of 'Thunder Cloud' are purple in color.

Plants of the new *Eremophila* can be compared to plants of *Eremophila maculata* 'Valentine', not patented. In side-by-side comparisons, plants of the new *Eremophila* differ primarily from plants of 'Valentine' in the following characteristics:

1. Plants of the new *Eremophila* are more rounded than and not as mounded as plants of 'Valentine'.
2. Leaves of plants of the new *Eremophila* are acicular whereas leaves of plants of 'Valentine' are oblong.
3. Flowers of plants of the new *Eremophila* are bright red in color whereas flowers of plants of 'Valentine' are magenta in color.

Plants of the new *Eremophila* can also be compared to plants of an unnamed selection of *Eremophila pterocarpa*, not patented, commercially referred to as Silvery Poverty Bush. In side-by-side comparisons, plants of the new *Eremophila* differ primarily from plants of the unnamed selection of *Eremophila pterocarpa* in the following characteristics:

1. Plants of the new *Eremophila* are more compact and much shorter than plants of the unnamed selection of *Eremophila pterocarpa*.
2. Leaves of plants of the new *Eremophila* are dark green in color whereas leaves of plants of the unnamed selection of *Eremophila pterocarpa* are silvery green in color.
3. Plants of the new *Eremophila* flower for a longer period of time than plants of the unnamed selection of *Eremophila pterocarpa*.
4. Flowers of plants of the new *Eremophila* are bright red in color whereas flowers of plants of the unnamed selection of *Eremophila pterocarpa* are pale salmon in color.

BRIEF DESCRIPTION OF THE PHOTOGRAPHS

The accompanying colored photographs illustrate the overall appearance of the new *Eremophila* plant showing the colors as true as it is reasonably possible to obtain in colored reproductions of this type. Colors in the photographs may differ slightly from the color values cited in the detailed botanical description which accurately describe the colors of the new *Eremophila* plant.

The photograph on the first sheet (FIG. 1) is a side perspective view of a typical flowering plant of 'MSWNErmas' grown in a container.

Figure 2:
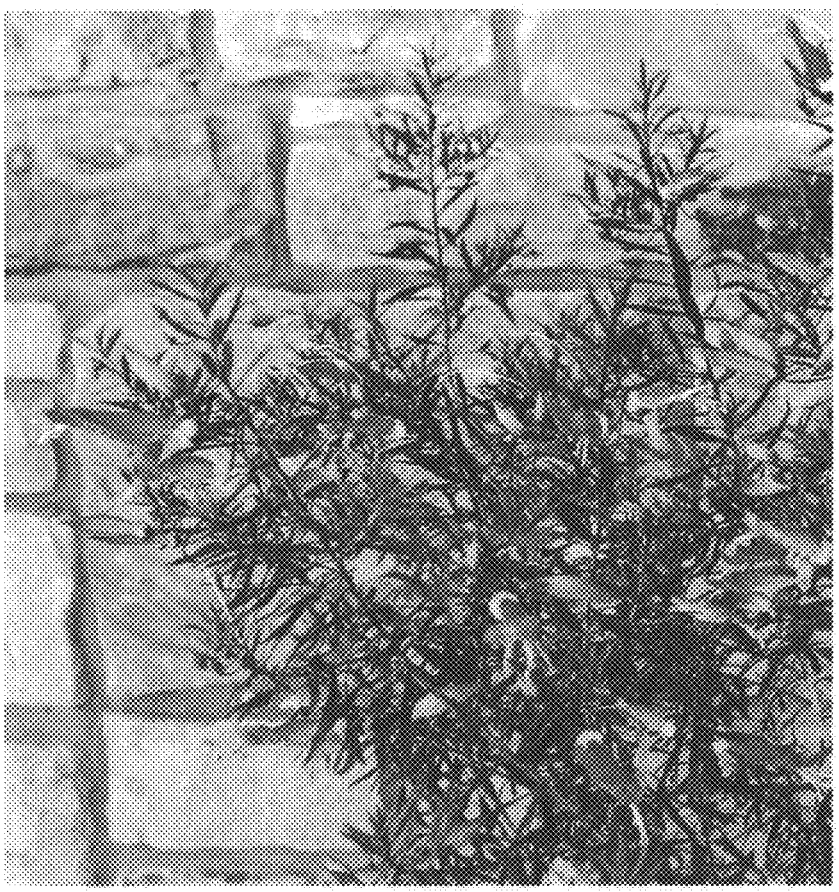

The photograph on the second sheet (FIG. 2) is a close-up view of a typical flowering plant of 'MSWNErmas'.

DETAILED BOTANICAL DESCRIPTION

The aforementioned photographs and following observations and measurements describe plants grown during the spring and summer in three-gallon containers in outdoor nurseries in Glendale, Ariz. and Fort Worth, Tex. and under cultural practices typical of commercial *Eremophila* production. During the production of the plants, day temperatures ranged from 10° C. to 47.8° C. and night temperatures ranged from 1° C. to 32.2° C. Plants were three years old when the photographs and description were taken. In the following description, color references are made to The Royal Horticultural Society Colour Chart, 2015 Edition, except where general terms of ordinary dictionary significance are used.

Botanical classification: *Eremophila maculata* 'MSWNErmas'.

Parentage:

*Female, or seed, parent.*—*Eremophila maculata* 'Thunder Cloud', not patented.

*Male, or pollen, parent.*—Unknown selection of *Eremophila maculata*, not patented.

Propagation:

*Type.*—By terminal vegetative cuttings.

*Time to initiate roots, summer.*—About 15 days at soil temperatures about 27° C.

*Time to initiate roots, winter.*—About 30 days at soil temperatures about 22° C.

*Time to produce a rooted young plant, summer.*—About 75 days at soil temperatures about 27° C.

*Time to produce a rooted young plant, winter.*—About 120 days at soil temperatures about 22° C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Perennial shrub; relatively compact, upright to outwardly spreading plant habit; vigorous growth habit and rapid growth rate; freely branching habit with lateral branches potentially developing at every node; dense and bushy appearance.

*Plant height.*—About 74 cm.

*Plant diameter.*—About 72 cm.

Lateral branch description:

*Length.*—About 53 cm.

*Diameter, proximally.*—About 1.5 cm.

*Internode length.*—Variably, about 1.5 cm to 3 cm.

*Strength.*—Moderately strong; flexible when developing.

*Aspect.*—Primary stems, mostly upright; lateral branches about 45° from primary stem axis.

*Texture and luster.*—Smooth, glabrous becoming rough and woody with development; semi-glossy when developing becoming matte with development.

*Color, developing.*—Close to 144A.

*Color, developed.*—Close to 199A; when woody, close to N199A.

Leaf description:

*Arrangement.*—Alternate, simple; sessile.

*Length.*—About 4.5 cm.

*Width.*—About 7.5 mm.

*Shape.*—Acicular.

*Apex.*—Acute.

*Base.*—Cuneate.

*Margin.*—Entire, slightly undulate.

*Texture and luster, upper and lower surfaces*.—Smooth, glabrous; slightly to semi-glossy.

*Venation pattern*.—Pinnate.

*Color*.—Developing leaves, upper and lower surfaces: Close to 144A becoming closer to more green than 146A. Fully expanded leaves, upper surface: More green than 147A; venation, more green than 147A. Fully expanded leaves, lower surface: Darker green than 146A; midvein, close to 146A and lateral venation, darker green than 146A.

Flower description:

*Flower arrangement and habit*.—Bilabiate flowers with a bulbous base; five fused petals; upper lip, four-parted and lower lip, single lobe; flowers face mostly outwardly; freely flowering habit with single flowers potentially developing at every axil during the flowering season.

*Fragrance*.—None detected.

*Natural flowering season*.—Plants flower continuously from spring until late summer in northern Texas.

*Flower longevity*.—Flowers last about two weeks on the plant; flowers persistent.

*Flower diameter* (*horizontal axis*).—About 1.25 cm.

*Flower height* (*vertical axis*).—About 2 cm.

*Flower depth* (*not including reproductive organs*).—About 4 cm.

*Flower throat diameter*.—About 1 cm.

*Flower tube length*.—About 1.6 cm.

*Flower tube diameter, distally*.—About 5 mm.

*Flower tube diameter, bulbous base*.—About 9 mm.

*Flower buds* (*prior to petal appearance*).—Length: About 9 mm. Diameter: About 3 mm. Shape: Narrowly ovoid. Texture and luster: Smooth, glabrous; semi-glossy. Color: Close to 146A; prior to petal opening, close to 151A variably overlain with close to between N45A and 46A.

*Petals*.—Arrangement: Five fused petals fused at the base; distally, upper lip is four-parted and reflexing; lower lip is a single lobe that is reflexing to curled. Length, upper lip, free part: About 3 cm. Length, lower lip, free part: About 2.7 cm. Width, upper lip, free part, flattened: About 1.6 cm. Width, lower lip, free part, flattened: About 6 mm. Shape, upper lip, free part: Broadly lanceolate; apices, acuminate. Shape, lower lip, free part: Lanceolate; apex, acuminate. Margin, upper lip, free part: Entire; reflexed. Margin, lower lip, free part: Entire; reflexed and curled. Texture and luster, upper and lower lips, free part, upper surface: Smooth, glabrous; semi-glossy. Texture and luster, upper and lower lips, free part, lower surface: Smooth, glabrous; semi-glossy to glossy. Texture and luster, throat: Sparsely pubescent; slightly to semi-glossy. Texture and luster, tube and bulbous base: Smooth, glabrous; semi-glossy to glossy. Color, free and fused portions: When opening and fully opened, inner surface: Close to 162B to 162C; spots, close to 59A; venation, similar to lamina; colors do not change with development. When opening and fully opened, outer surface: Close to 151B to 151C variably overlain with close to 59A; venation, similar to lamina; colors do not change with development; bulbous base, close to N144B.

*Sepals*.—Arrangement: Star-shaped calyx with five sepals in a single whorl fused at the base. Length: About 7 mm. Width, free part: About 4.5 mm. Shape: Narrowly deltoid. Apex: Elongated acuminate. Margin: Entire. Texture and luster, upper surface: Smooth, glabrous; slightly glossy. Texture and luster, lower surface: Smooth, glabrous; semi- glossy. Color: When opening and fully opened, upper surface: Close to 146A. When opening and fully opened, lower surface: Close to 146A.

*Peduncles*.—Length: About 1.75 mm. Diameter: About 1 mm. Angle: About 45° from stein axis. Strength: Moderately strong, flexible, wiry. Texture and luster: Smooth, glabrous; semi-glossy. Color: Close to 144A variably overlain with close to 187A.

*Reproductive organs*.—Stamens: Quantity: Four to five per flower. Filament length: About 3.5 cm. Filament color: Close to between 154D and 157A. Anther size: About 1.5 mm by 3 mm. Anther shape: Bi-lobed, oblong. Anther color: Close to 163A. Pollen amount: None observed. Pistils: Quantity: One per flower. Pistil length: About 5 cm. Style length: About 4.7 cm. Style color: Close to NN155D. Stigma diameter: Less than 1 mm. Stigma shape: Tapering. Stigma color: Close to NN155D. Ovary color: Close to 144A.

*Fruits*.—Quantity per flower: One. Size and shape: About 1.1 cm by 1.2 cm; roughly spherical. Texture and luster: Smooth, glabrous; semi-glossy. Color: More green than 144A.

*Seeds*.—Quantity per fruit: Typically one or two. Size and shape: About 2 mm by 2.5 mm; bi-lobed. Texture and luster: Smooth, glabrous; semi-glossy. Color: More green than 144A.

Pathogen resistance: To date, plants of the new *Eremophila* have not been observed to be resistant to pathogens common to *Eremophila* plants.

Garden performance: Plants of the new *Eremophila* have been observed to have good garden performance, to tolerate drought, arid conditions and temperatures ranging from −6.7° C. to 47.8° C.

It is claimed:

1. A new and distinct *Eremophila* plant named 'MSWN-Ermas' as illustrated and described.

* * * * *